US007276216B2

(12) United States Patent
Segelke et al.

(10) Patent No.: US 7,276,216 B2
(45) Date of Patent: Oct. 2, 2007

(54) PROTEIN CRYSTALLOGRAPHY PRESCREEN KIT

(75) Inventors: Brent W. Segelke, San Ramon, CA (US); Heike I. Krupka, Livermore, CA (US); Bernhard Rupp, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 127 days.

(21) Appl. No.: 11/084,479

(22) Filed: Mar. 17, 2005

(65) Prior Publication Data

US 2005/0205006 A1    Sep. 22, 2005

Related U.S. Application Data

(62) Division of application No. 10/218,764, filed on Aug. 14, 2002, now Pat. No. 6,916,455.

(51) Int. Cl.
 *B01D 9/02*  (2006.01)
(52) U.S. Cl. .......................................... 422/245; 422/64
(58) Field of Classification Search ............. 422/245.1, 422/64
See application file for complete search history.

(56) References Cited

U.S. PATENT DOCUMENTS 5,525,198 A    6/1996  Craig et al.
5,597,457 A    1/1997  Craig et al.
6,193,933 B1 *  2/2001  Sasaki et al. ................. 422/64
6,267,935 B1   7/2001  Hol et al.
6,451,591 B1 *  9/2002  Edwards .................. 435/305.2
6,632,655 B1 * 10/2003  Mehta et al. ............ 435/288.5

FOREIGN PATENT DOCUMENTS

JP    2000225166    *  7/2000

OTHER PUBLICATIONS

No author, Quik Screen, "Sodium/Potassium Phosphate," Hampton Research Corporation web site, www.hamptonresearch.com, 2000, 2 pages.

* cited by examiner

*Primary Examiner*—Felisa Hiteshew
(74) *Attorney, Agent, or Firm*—Eddie E. Scott; John H. Lee

(57) ABSTRACT

A kit for prescreening protein concentration for crystallization includes a multiplicity of vials, a multiplicity of preselected reagents, and a multiplicity of sample plates. The reagents and a corresponding multiplicity of samples of the protein in solutions of varying concentrations are placed on sample plates. The sample plates containing the reagents and samples are incubated. After incubation the sample plates are examined to determine which of the sample concentrations are too low and which the sample concentrations are too high. The sample concentrations that are optimal for protein crystallization are selected and used.

22 Claims, 4 Drawing Sheets

PROTEIN CRYSTALLOGRAPHY PRESCREEN KIT

CROSS-REFERENCE TO RELATED APPLICATIONS

This application is a division of application Ser. No. 10/218,764 filed Aug. 14, 2002, now U.S. Pat. No. 6,916,455, entitled "Protein Crystallography Prescreen Kit" by inventors Brent W. Segelke, Heike I. Krupka, and Bernhard Rupp.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to X-ray crystallography and more particularly to macromolecular crystallization screening.

2. State of Technology

U.S. Pat. No. 5,597,457 for a system and method for forming synthetic protein crystals to determine the conformational structure by crystallography to George D. Craig, issued Jan. 28, 1997, provides the following background information, "The conformational structure of proteins is a key to understanding their biological functions and to ultimately designing new drug therapies. The conformational structures of proteins are conventionally determined by x-ray diffraction from their crystals. Unfortunately, growing protein crystals of sufficient high quality is very difficult in most cases, and such difficulty is the main limiting factor in the scientific determination and identification of the structures of protein samples. Prior art methods for growing protein crystals from super-saturated solutions are tedious and time-consuming, and less than two percent of the over 100,000 different proteins have been grown as crystals suitable for x-ray diffraction studies."

U.S. Pat. No. 6,267,935 for crystallization media to Wim G. J. Hol, issued Jul. 31, 2001, provides the following background information, "The process of growing biological macromolecule crystals remains, however, a highly empirical process. Macromolecular crystallization is dependent on a host of experimental parameters, including; pH, temperature, the concentration of salts in the crystallization drop, the concentration of the macromolecule to be crystallized, and the concentration of the precipitating agent (of which there are hundreds). In particular, the choice of solute conditions in which to grow crystals continues to be a matter for empirical determination. Consequently, the ability to rapidly and easily generate many crystallization trials is important in determining the ideal conditions for crystallization. Thus, there is a need for sets of preformulated crystallization solutions that can be used to rapidly and easily generate many crystallization trials."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

X-ray crystallography is a technique that exploits the fact that X-rays are diffracted by crystals. Growing protein crystals of sufficient high quality for X-ray crystallography is very difficult. One embodiment of the present invention is a kit for prescreening protein concentration for crystallization. The kit includes a multiplicity of vials, a multiplicity of reagents, a multiplicity of sample plates, and instructions for using the vials, the reagents, and the sample plates for assessing the proper protein concentration to carry out protein crystallization. One embodiment of the present invention provides a method of sample preparation for protein crystallization. It comprises steps for prescreening samples of a protein in a solution to assess the proper protein/solution concentration to carry out protein crystallization and X-ray crystallography. A multiplicity of preselected reagents are placed on a multiplicity of sample plates. A multiplicity of samples of the protein in a solution in varying concentrations are placed on the multiplicity of sample plates. The multiplicity of sample plates containing the multiplicity of reagents and the samples are incubated. The multiplicity of sample plates containing the multiplicity of reagents and the samples are examined to determine which of the sample concentrations are too low and which the sample concentrations are too high. The sample concentrations that are optimal for protein crystallization are selected and used.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
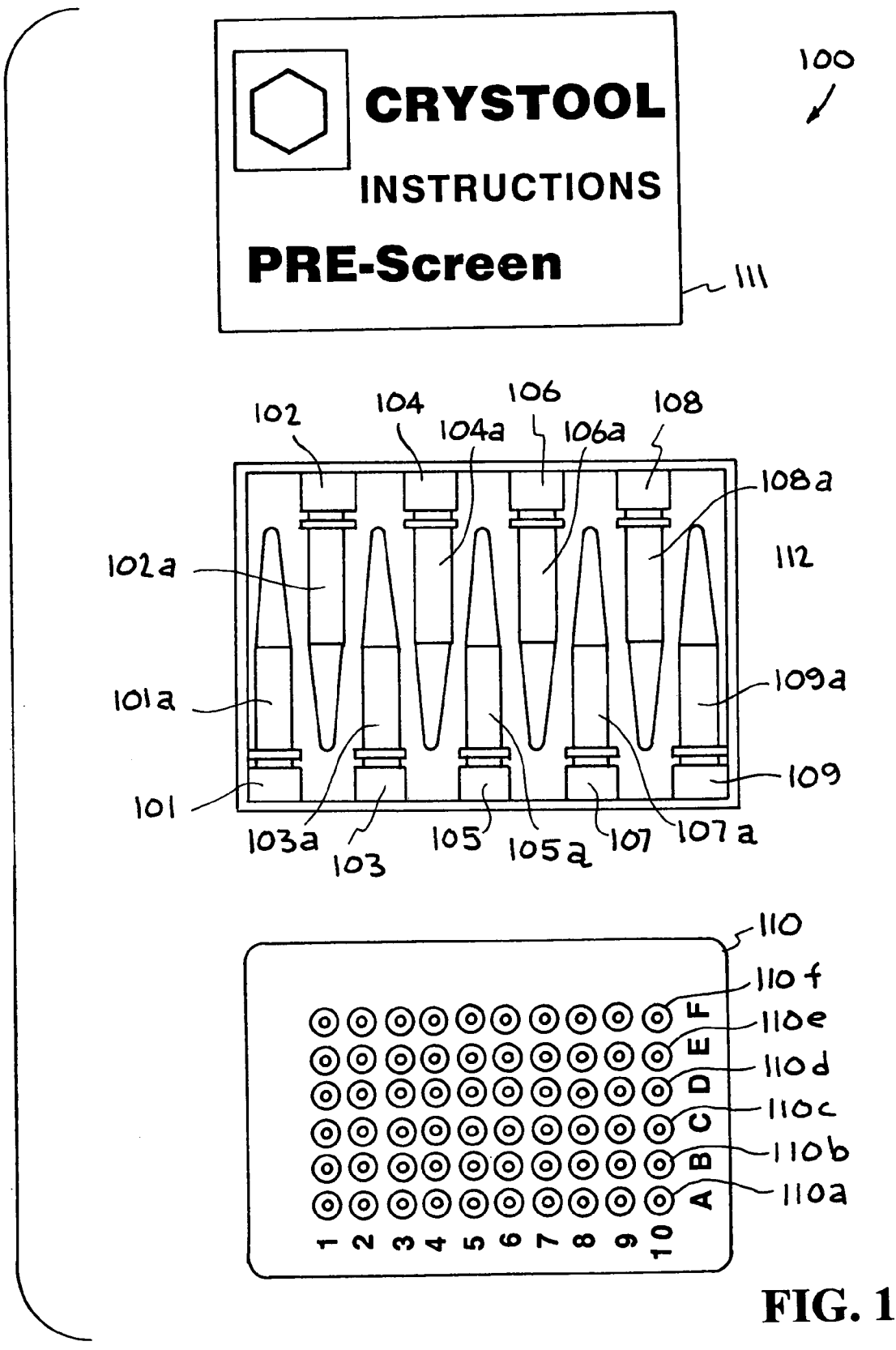
FIG. 1 shows one embodiment of a kit for prescreening protein concentration for crystallization.

Referring now to the drawings, to the following detailed information, and to incorporated materials; a detailed description of the invention, including specific embodiments, is presented. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to FIG. 1, a kit for prescreening protein concentration for crystallization is illustrated. The kit is designated generally by the reference numeral 100. The kit 100 includes a multiplicity of vials 101 through 109, a multiplicity of reagents 101A through 109A, and a multiplicity of sample plates 110A through 110G. Instructions 111 for using the vials, the reagents, and the sample plates for assessing the proper protein concentration to carry out protein crystallization are included. The vials 101 through 109 containing reagents 101A through 109A, Terazaki plate 110 containing sample plates 110A through 110G, and instructions 111 are packed in a cardboard box 112.

In order to obtain a crystal, the protein molecules must assemble into a periodic lattice. It is generally desirable to starts with a solution of the protein with a fairly high concentration (2-50 mg/ml) and add reagents that reduce the solubility close to spontaneous precipitation. By slow further concentration, and under conditions suitable for the formation of a few nucleation sites, small crystals may start to grow. Often very many conditions have to be tried to succeed. This is done by initial screening, followed by a systematic optimization of conditions. Crystals should to be a few tenths of a mm in each direction to be useful for diffraction experiments.

The kit 100 aids the macromolecular crystal grower in selecting protein concentrations suitable for crystallization experiments. Likelihood of success and overall efficiency increase through selection of promising protein concentrations. The kit 100 contains nine 1.5 ml Eppendorf cryo-vials 101 through 109. The nine vials are labeled with cryo-babies labels.

The kit 100 includes nine different reagents 101A through 109A that are precisely formulated and consist of high quality chemicals of per analysis grade to ensure reliable performance. The reagents in kit 100 are 101A—50% PEG 4000, 102A—30% PEG 4000, 103A—5% PEG 4000, 104A—3M Ammonium Sulfate, 105A—2M Ammonium Sulfate, 106A—0.5M Ammonium Sulfate, 107A—40% Isopropanol, 108A—30% Isopropanol, 109A—5% Isopropanol. All reagents are aqueous solutions containing 0.1M Tris/HCl buffer at pH 8.5. One ml of each reagent is provided in the 1.5 ml Eppendorf cryo-vials 101 through 109.

The kit 100 contains a 70-well Terazaki plate 110. The Terazaki plate 110 includes 10 individual row of sample plates 110A through 110G.s The Terazaki plate 110 can be obtained from Robbins Scientific, or Hampton (Order No. 1004-00-0 at Robbins Scientific, or Hampton HR3-120).

The kit 100 contains instructions 111 for using the vials, the reagents, and the sample plates for assessing the proper protein concentration to carry out protein crystallization are included. The instructions 111 include the following statements:

Protein Prescreen Setup:
1. Set up 3 rows of 3 1 µl drops of your protein at the starting concentration in the Terazaki plate
2. Add 1 µl each of the nine PRE-Screen reagents to your protein on the Terazaki plate (reagent 1-3 to the first row, reagent 4-6 to the second row, reagent 7-9 to the third row), mix by pipetting up and down one or two times
3. Incubate for at least 1 min—you do not need to cover the plate
4. View your results under the microscope and note your observations of each experiment.

How to Evaluate your Results:
If every drop remains clear after 1-5 min, your protein concentration is too low, you should concentrate your protein. If on the other hand every drop contains heavy precipitate, your protein concentration is clearly too high,
and the protein should be diluted with a suitable buffer. After you have adjusted your protein concentration, you should verify by repeating the PRE-Screen that precipitation is induced at a modest number of conditions (perhaps 3-6). This tells you that you have a reached a concentration range optimal for crystallization screening.

Figure 2:
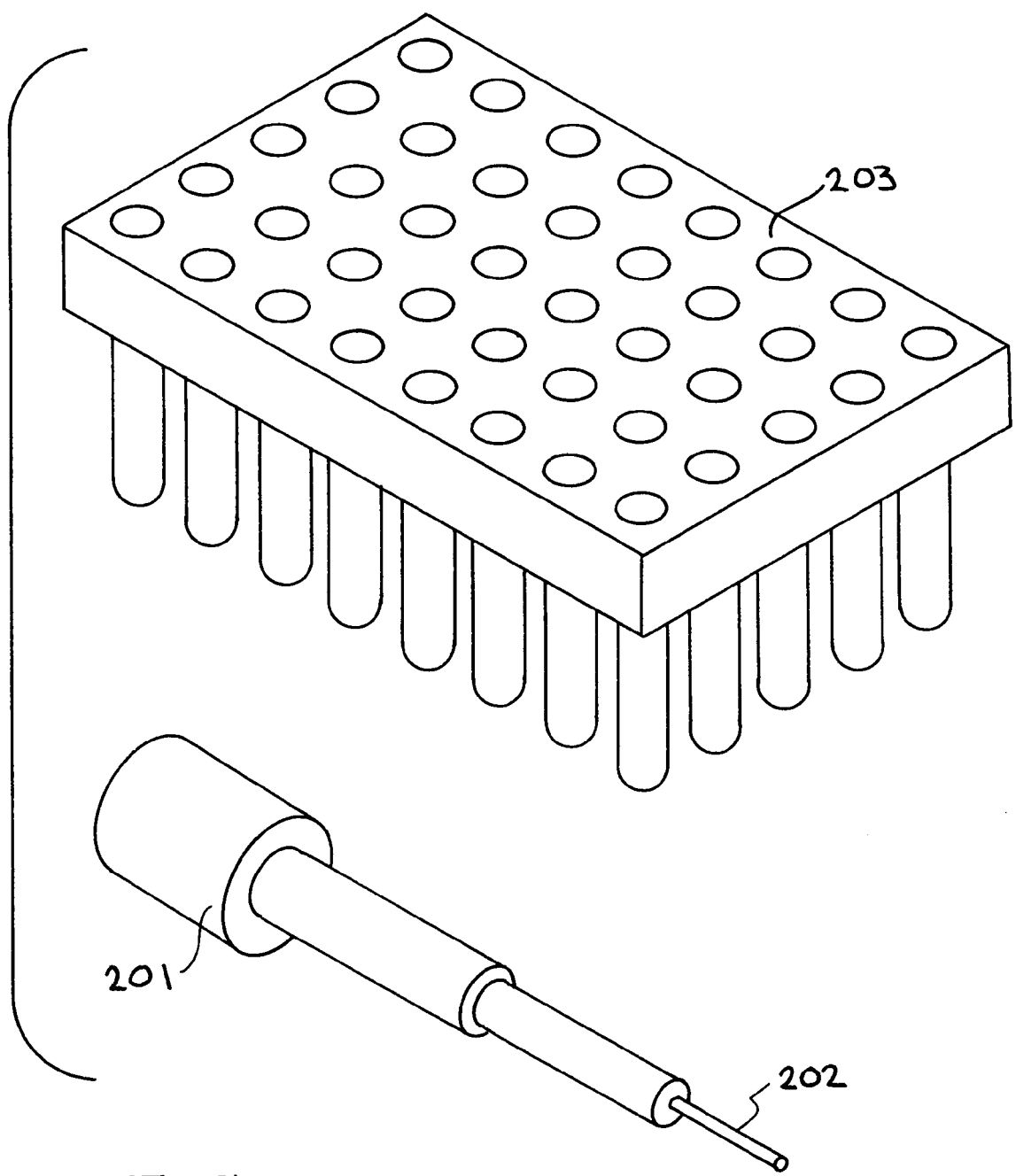
FIG. 2 shows some of the equipment that can be used with the kit for prescreening protein concentration for crystallization.

Referring now to FIG. 2, some of the equipment that can be used with the kit 100 is shown. The additional equipment includes a pipette suitable 201 for pipetting 1 µl volumes, tips 202, and a sample rack 203. A light microscope can be used. The protein crystallography prescreen kit 100 is a reagent kit designed to aid the macromolecular crystal grower in the set up of successful crystallization experiments.

The sample is initially provided as a protein stock solution in minimal buffer (typically 10 mM buffer and 50 mM KCl and no phosphate), at some reasonably achievable starting concentration. An example of use of the protein prescreen setup includes the following steps: (1) Set up 3 rows of 3 1 µl drops of the protein at the starting concentration in the Terazaki plate 110, (2) Add 1 µl each of the nine reagents 101A through 109A to the protein on the Terazaki plate 110 (reagent 1-3 to the first row, reagent 4-6 to the second row, reagent 7-9 to the third row), mix by pipetting up and down one or two times, (3) incubate for at least 1 min—it is not necessary to cover the plate, and (4) view the results under the microscope and note observations of each experiment. If every drop remains clear after 1-5 min, the protein concentration is too low. The protein sample should be concentrated. If on the other hand every drop contains heavy precipitate, the protein concentration is too high, and the protein should be diluted with a suitable buffer. After the protein concentration has been adjusted, the test should be verified by repeating the prescreen test that precipitation is induced at a modest number of conditions (perhaps 3-6). This indicates that a concentration range has been reached that is optimal for crystallization screening.

The kit 100 is used by macromolecular crystallographers to assess the proper protein concentration to carry out protein crystallization. The handling of the kit 100 is easy and comprehensive and results occur within minutes. Typically 1 L1 of the kit 10 is mixed with 1Al of protein of various concentrations on the Terasaki plate. The drops should be controlled after 1-5 min incubation time under a light microscope. If all nine reagents produce clear drops, the protein concentration is too low, if all nine reagents produce heavy precipitant, turning the drop opaque, the protein concentration is too high for protein crystallization to occur. With this method the concentration range that will most likely lead to successful protein crystal formation can be determined easily and quickly.

Figure 3:
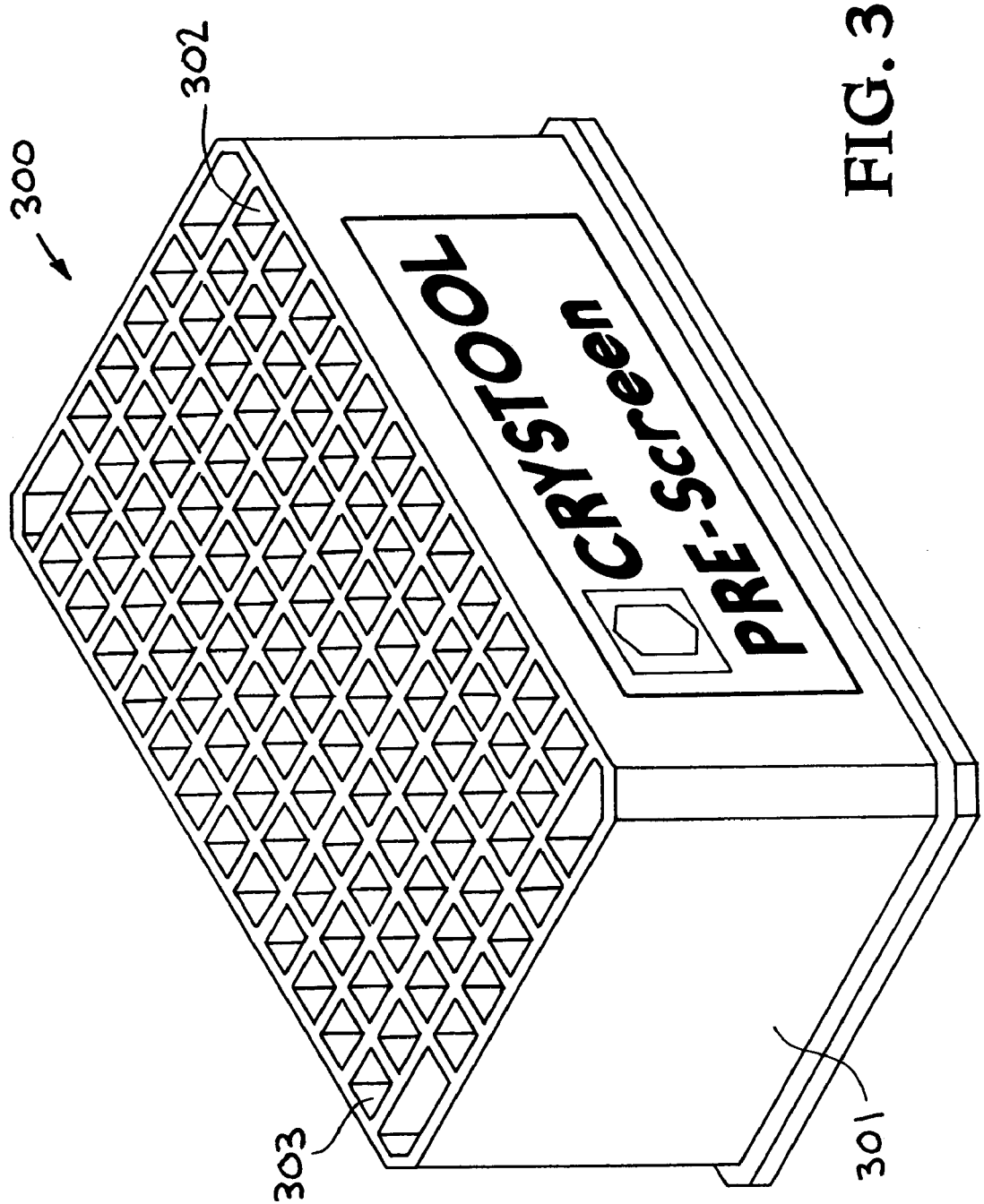
FIG. 3 shows another embodiment of a kit for prescreening protein concentration for crystallization.

Referring now to FIG. 3, another embodiment of a kit for prescreening protein concentration for crystallization is illustrated. This embodiment of a kit for prescreening protein concentration for crystallization is designated generally by the reference numeral 300. X-ray crystallography is a technique that exploits the fact that X-rays are diffracted by crystals. Growing protein crystals of sufficient high quality for X-ray crystallography is very difficult. The kit 300 aids the macromolecular crystal grower in selecting protein concentrations suitable for crystallization experiments.

A 96-well deep-well block 301 is shown in FIG. 3. The 96-well deep-well block 301 is pre-arrayed for ease of automation. The 96-well deep-well block 301 is included in kit 300. The kit 300 is moderately expanded to 12 reagent conditions to be tested against the protein of interest. The 12 reagent conditions test 4 broad chemistries at each of three concentrations to bracket the solubility behavior of the protein of interest against these chemistries. There are 8 copies (1 in each row 302 of the deep-well block 301) of the kit 300 for use with as many as 8 proteins of interest to be tested simultaneously for high throughput screening. The block 301 includes long row 303 with 12 spaces. Twelve vials similar to the vials 101 through 109 shown in FIG. 1 are included in kit 300. The twelve vials contain reagents. The kit 300 also includes a plate containing sample plates and instructions packed in a cardboard box.

The instructions provide a method of sample preparation for protein crystallization and X-ray crystallography. The instructions set out a number of steps including prescreening samples of a protein in a solution to assess the proper protein/solution concentration to carry out protein crystallization; placing a multiplicity of pre-selected reagents on a multiplicity of sample plates; placing a multiplicity of samples of the protein in a solution in varying concentrations on the multiplicity of sample plates; incubating the multiplicity of sample plates containing the multiplicity of reagents and the samples, viewing the multiplicity of sample plates containing the multiplicity of reagents and the samples to determine which of the sample concentrations are too low and which the sample concentrations are too high, and selecting the sample concentrations that are optimal for protein crystallization.

Figure 4:
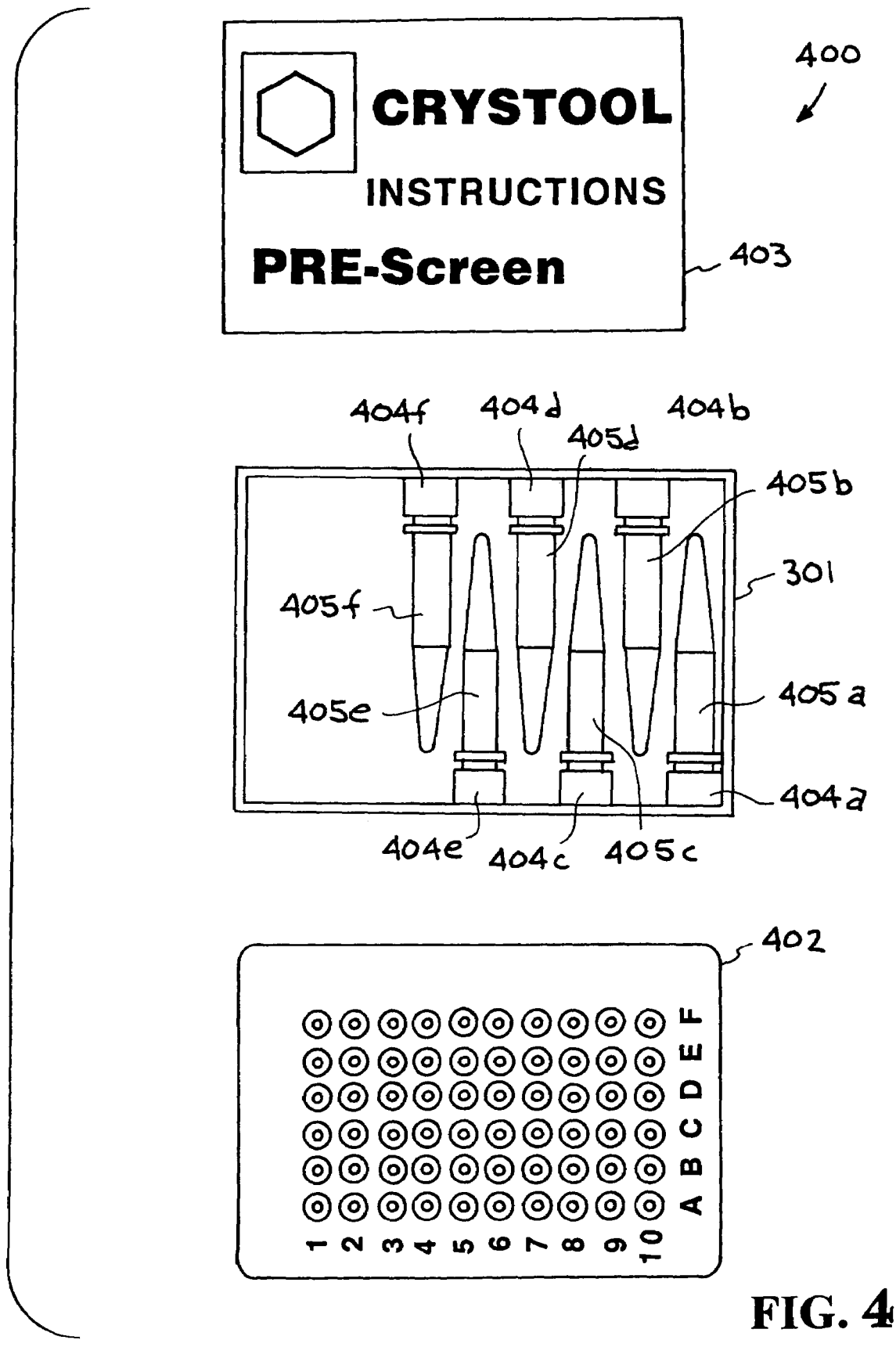
FIG. 4 shows yet another embodiment of kit for prescreening protein concentration for crystallization.

Referring now to FIG. 4, another embodiment of a kit for prescreening protein concentration for crystallization is illustrated. This embodiment of a kit for prescreening protein concentration for crystallization is designated generally by the reference numeral 400. The lit 400 includes a box 301 of vials, a plate 402, and instructions 303. The kit 400 is similar to kit 100 shown in FIG. 1; however, kit 400 has 6 vials instead of the 9 vials of kit 100. The physical appearance of kit 100 and kit 400 be nearly identical; however, there are fewer conditions to test with kit 400 and therefore fewer vials.

X-ray crystallography is a technique that exploits the fact that X-rays are diffracted by crystals. Growing protein crystals of sufficient high quality for X-ray crystallography is very difficult. The kit 400 aids the macromolecular crystal grower in selecting protein concentrations suitable for crystallization experiments. The kit 400 includes a multiplicity of vials 404A, 404B, 404C, etc. containing a multiplicity of reagents 405A, 405B, 405C, etc. and the Terazaki plate 404 containing individual sample plates.

The instructions 403 provide a method of sample preparation for protein crystallization and X-ray crystallography. The instructions set out a number of steps including prescreening samples of a protein in a solution to assess the proper protein/solution concentration to carry out protein crystallization; placing a multiplicity of pre-selected reagents on a multiplicity of sample plates; placing a multiplicity of samples of the protein in a solution in varying concentrations on the multiplicity of sample plates; incubating the multiplicity of sample plates containing the multiplicity of reagents and the samples, viewing the multiplicity of sample plates containing the multiplicity of reagents and the samples to determine which of the sample concentrations are too low and which the sample concentrations are too high, and selecting the sample concentrations that are optimal for protein crystallization.

The kit 400 comes as a reduced set of reagents from the kit 100 shown in FIG. 1. The kit 400 is derived from observed correlations between crystallization success and results from the kit 100 shown in FIG. 1. Applicants have accumulated data of both the prescreen results and the crystallization success for proteins and derived a subset of conditions from which crystallization results are best predicted. Applicants have accumulated results of the prescreen and subsequent crystallization trials of ~70 protein samples. Prescreen results were checked versus the crystallization success rate (that means the number of crystallization experiments that yielded crystals for a given sample divided by the number of experiments set up for that sample) and the prescreen conditions and results were picked that correlate most strongly with the success rate. The advantage is that the prescreen will be more predictive of crystallization success and it will require less material. New prescreen condition can be introduced specifically to test them against crystallization success thereby refining the prescreen over time.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A kit for prescreening protein concentration for crystallization, comprising:
   a multiplicity of cryo-vials,
   a multiplicity of reagents,
   a multiplicity of sample plates, and
   instructions for using said vials, said reagents, and said sample plates for assessing the proper protein concentration to carry out protein crystallization.

2. The kit for prescreening protein concentration for crystallization of claim 1, wherein said multiplicity of cryo-vials are Eppendorf cryo-vials.

3. The kit for prescreening protein concentration for crystallization of claim 2, wherein said multiplicity of Eppendorf cryo-vials are 1.5 ml. Eppendorf cryo-vials.

4. The kit for prescreening protein concentration for crystallization of claim 1, wherein said vials are labeled.

5. The kit for prescreening protein concentration for crystallization of claim 4, wherein said vials are labeled with cryo-babies labels.

6. The kit for prescreening protein concentration for crystallization of claim 1, wherein said multiplicity of reagents are precisely formulated and consist of high quality chemicals of per analysis grade chemicals.

7. The kit for prescreening protein concentration for crystallization of claim 6, wherein said multiplicity of reagents are aqueous solutions containing 0.1M Tris/HCl buffer at pH 8.5.

8. The kit for prescreening protein concentration for crystallization of claim 1, wherein said multiplicity of reagents includes a reagent of 50% PEG 4000.

9. The kit for prescreening protein concentration for crystallization of claim 1, wherein said multiplicity of reagents includes a reagent of 30% PEG 4000.

10. The kit for prescreening protein concentration for crystallization of claim 1, wherein said multiplicity of reagents includes a reagent of 5% PEG 4000.

11. The kit for prescreening protein concentration for crystallization of claim 1, wherein said multiplicity of reagents includes a reagent of 3M Ammonium Sulfate.

12. The kit for prescreening protein concentration for crystallization of claim 1, wherein said multiplicity of reagents includes a reagent of 2M Ammonium Sulfate.

13. The kit for prescreening protein concentration for crystallization of claim 1, wherein said multiplicity of reagents includes a reagent of 0.5M Ammonium Sulfate.

14. The kit for prescreening protein concentration for crystallization of claim 1, wherein said multiplicity of reagents includes a reagent of 40% Isopropanol.

15. The kit for prescreening protein concentration for crystallization of claim 1, wherein said multiplicity of reagents includes a reagent of 30% Isopropanol.

16. The kit for prescreening protein concentration for crystallization of claim 1, wherein said multiplicity of reagents includes a reagent of 5% Isopropanol.

17. The kit for prescreening protein concentration for crystallization of claim 1, wherein said multiplicity of reagents include a first reagent of 50% PEG 4000, a second reagent of 30% PEG 4000, a third reagent of 5% PEG 4000, a fourth reagent of 3M Ammonium Sulfate, a fifth reagent of 2M Ammonium Sulfate, a sixth reagent of 0.5M Ammonium Sulfate, a seventh reagent of 40% Isopropanol, an eight reagent of 30% Isopropanol, and a ninth reagent of 5% Isopropanol.

18. The kit for prescreening protein concentration for crystallization of claim 1, wherein said instructions include directions for mixing reagents with a protein sample.

19. The kit for prescreening protein concentration for crystallization of claim 18, wherein said instructions include directions to mix 1 L1 of said reagents with 1Al of said protein sample in drops of various concentrations on said plates.

20. The kit for prescreening protein concentration for crystallization of claim 19, wherein said instructions include directions to control said drops after 1-5 min incubation time under a light microscope.

21. The kit for prescreening protein concentration for crystallization of claim 1, wherein said instructions indicate that if all reagents produce clear drops the protein concentration is too low, and if all reagents produce heavy precipitant, turning the drop opaque, the protein concentration is too high for protein crystallization to occur.

22. The kit for prescreening protein concentration for crystallization of claim 1, wherein said multiplicity of vials, said multiplicity of reagents, said multiplicity of sample plates, and said instructions are packed in a container.

* * * * *